United States Patent
Filiberti et al.

(10) Patent No.: US 11,717,238 B2
(45) Date of Patent: Aug. 8, 2023

(54) COUCH TOP EXTENSION FOR RADIATION THERAPY AND IMAGING

(71) Applicant: Varian Medical Systems International AG, Steinhausen (CH)

(72) Inventors: Reto W. Filiberti, Baar (CH); Martin Feusi, Greifensee (CH); Niklaus Schär, Wikon (CH); Christoph Müller, Lengnau (CH)

(73) Assignee: Siemens Healthineers International AG, Steinhausen (CH)

( * ) Notice: Subject to any disclaimer, the term of this patent is extended or adjusted under 35 U.S.C. 154(b) by 558 days.

(21) Appl. No.: 16/714,753

(22) Filed: Dec. 15, 2019

(65) Prior Publication Data

US 2021/0177362 A1 Jun. 17, 2021

(51) Int. Cl.

| A61B 6/04 | (2006.01) |
|---|---|
| A61B 6/00 | (2006.01) |
| A61G 7/05 | (2006.01) |
| A61G 13/12 | (2006.01) |
| A61G 13/10 | (2006.01) |

(52) U.S. Cl.
CPC .............. *A61B 6/0407* (2013.01); *A61B 6/44* (2013.01); *A61B 6/46* (2013.01); *A61G 7/05* (2013.01); *A61G 13/10* (2013.01); *A61G 13/129* (2013.01); *A61G 13/1285* (2013.01)

(58) Field of Classification Search
CPC .......... A61B 6/0407; A61B 6/44; A61B 6/46; A61B 6/0492; A61B 5/055; A61G 7/05; A61G 13/1285; A61G 13/129; A61G 13/101; A61G 13/10; A61G 2205/60; A61N 5/1049; A61N 2005/1097; Y10S 439/95; Y10S 439/928; H02J 50/10; H02J 7/025; F16B 5/0084; F16B 5/0088; H01F 7/00

See application file for complete search history.

(56) References Cited

U.S. PATENT DOCUMENTS

| 5,851,182 | A | 12/1998 | Sahadevan |
| 6,941,599 | B2 * | 9/2005 | Zacharopoulos ........ A61B 6/04 5/601 |
| 7,076,821 | B2 | 7/2006 | de Mooy |
| 9,179,880 | B2 | 11/2015 | Coppens |

(Continued)

FOREIGN PATENT DOCUMENTS

| EP | 1009284 A1 | 6/2000 | |
| WO | 9911176 A1 | 3/1999 | |
| WO | WO-9911176 A1 * | 3/1999 | ........... A61B 6/0421 |

OTHER PUBLICATIONS

"Array." Merriam-Webster, Merriam-Webster, www.merriam-webster.com/dictionary/array.*

(Continued)

*Primary Examiner* — David R Hare
*Assistant Examiner* — Madison Emanski
(74) *Attorney, Agent, or Firm* — Harness, Dickey & Pierce, P.L.C.

(57) ABSTRACT

A couch top extension includes a first section and a second section extending from the first section. The first section has a varying shape profile and the second section has a substantially uniform shape profile. A couch top extension includes an extension board comprising one or more identifiers capable of providing a detectable signal indicative of an identification of the extension board.

20 Claims, 18 Drawing Sheets

(56) References Cited

U.S. PATENT DOCUMENTS

| | | | | |
|---|---|---|---|---|
| 9,662,256 | B2* | 5/2017 | Marle | A61B 6/4494 |
| 2004/0199072 | A1* | 10/2004 | Sprouse | A61B 5/062 |
| | | | | 5/601 |
| 2007/0214570 | A1* | 9/2007 | Coppens | A61G 13/10 |
| | | | | 5/601 |
| 2008/0154124 | A1* | 6/2008 | Iustin | A61N 5/1049 |
| | | | | 600/424 |
| 2009/0129556 | A1* | 5/2009 | Ahn | A61N 5/1049 |
| | | | | 378/208 |
| 2010/0292559 | A1* | 11/2010 | Hannemann | G01S 13/88 |
| | | | | 600/407 |
| 2013/0312184 | A1* | 11/2013 | Wilson | A61B 6/0442 |
| | | | | 5/613 |
| 2014/0121497 | A1* | 5/2014 | Coppens | B32B 3/14 |
| | | | | 156/60 |
| 2018/0085603 | A1 | 3/2018 | Kruesi | |
| 2018/0140221 | A1* | 5/2018 | Weber | A61N 5/1049 |
| 2018/0344559 | A1* | 12/2018 | Hoel | B60B 33/0018 |

OTHER PUBLICATIONS

"Detect." Merriam-Webster, Merriam-Webster, www.merriam-webster.com/dictionary/detect.*

"Pattern." Merriam-Webster, Merriam-Webster, www.merriam-webster.com/dictionary/pattern.*

"Uniform." Merriam-Webster, Merriam-Webster, www.merriam-webster.com/dictionary/uniform.*

"Sensor." Dictionary, Cambridge, https://dictionary.cambridge.org/us/dictionary/english/sensor?q=sensor+.*

"Cross Section." Merriam-Webster, Merriam-Webster, www.merriam-webster.com/dictionary/cross%20section.*

PCT, International Search Report and Written Opinion of the Internal Searching Authority in PCT/EP/2020/085027, dated May 18, 2021, 16 pages.

PCT, Invitation to Pay Additional Fees and, Where Applicable, Protect Fee in International Application No. PCT/EP2020/085027, dated Mar. 16, 2021, 11 pages.

* cited by examiner

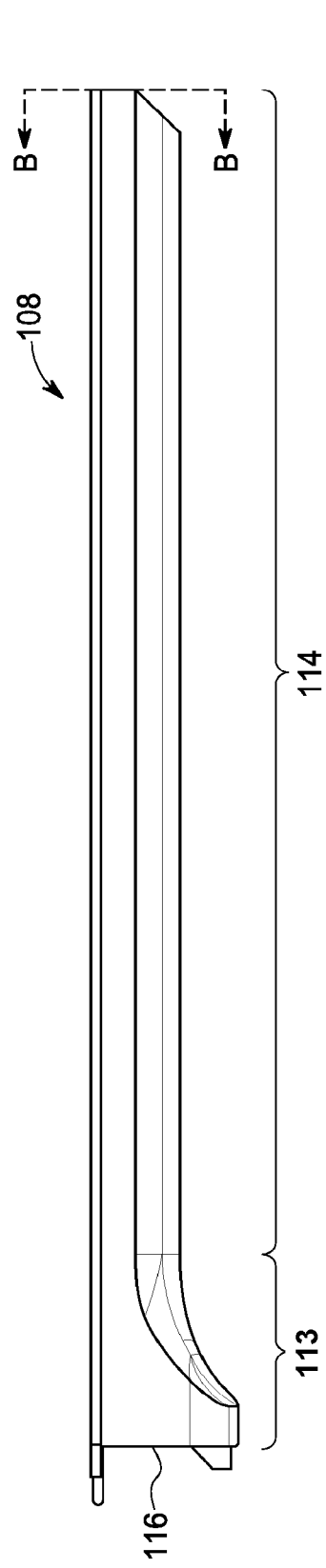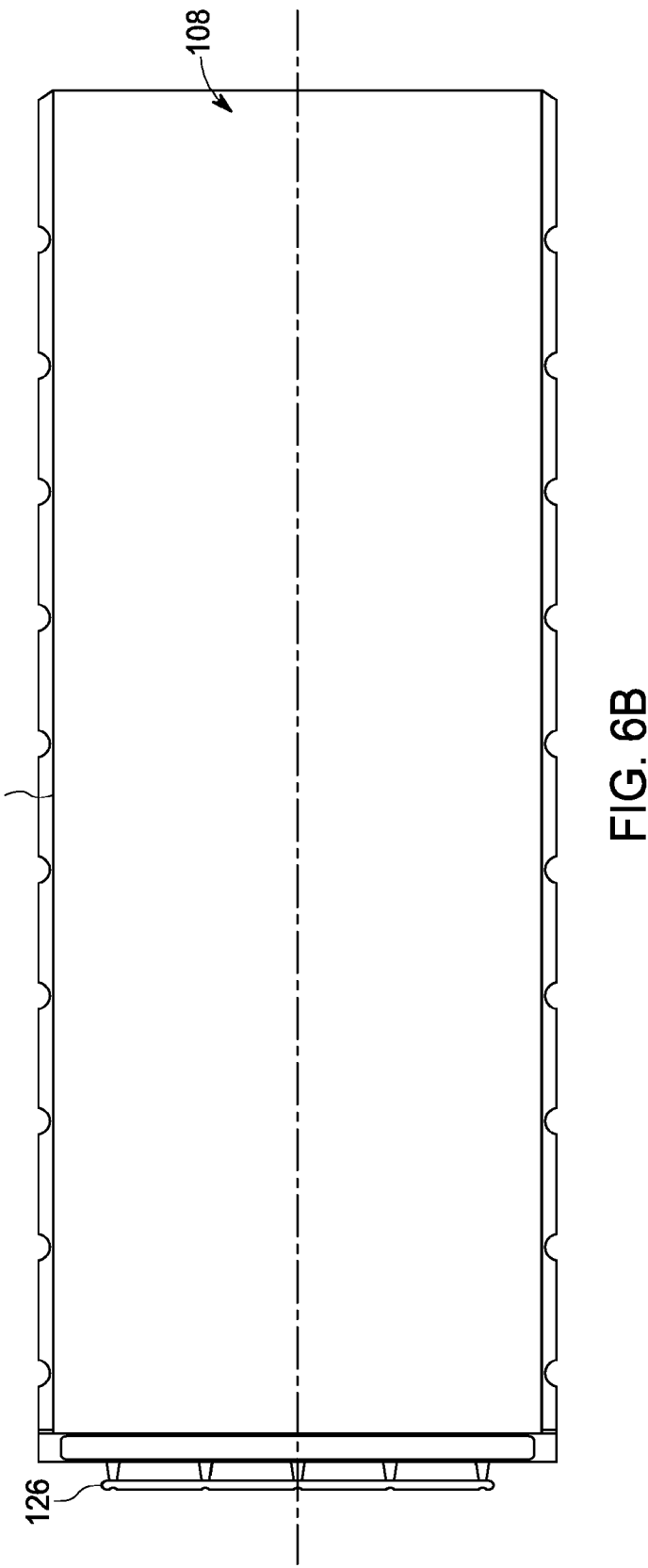
FIG. 6A
FIG. 6B

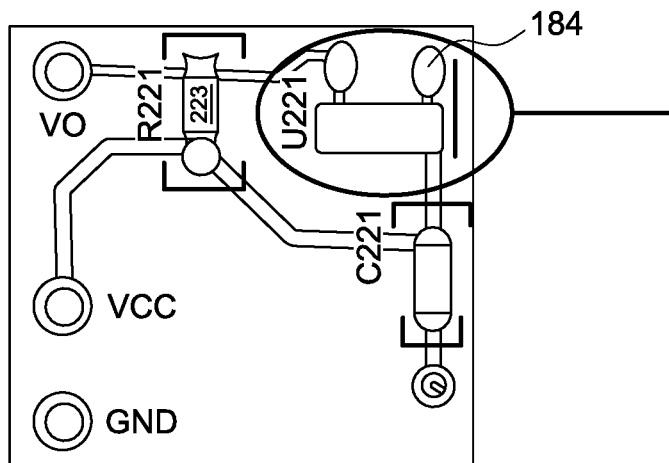
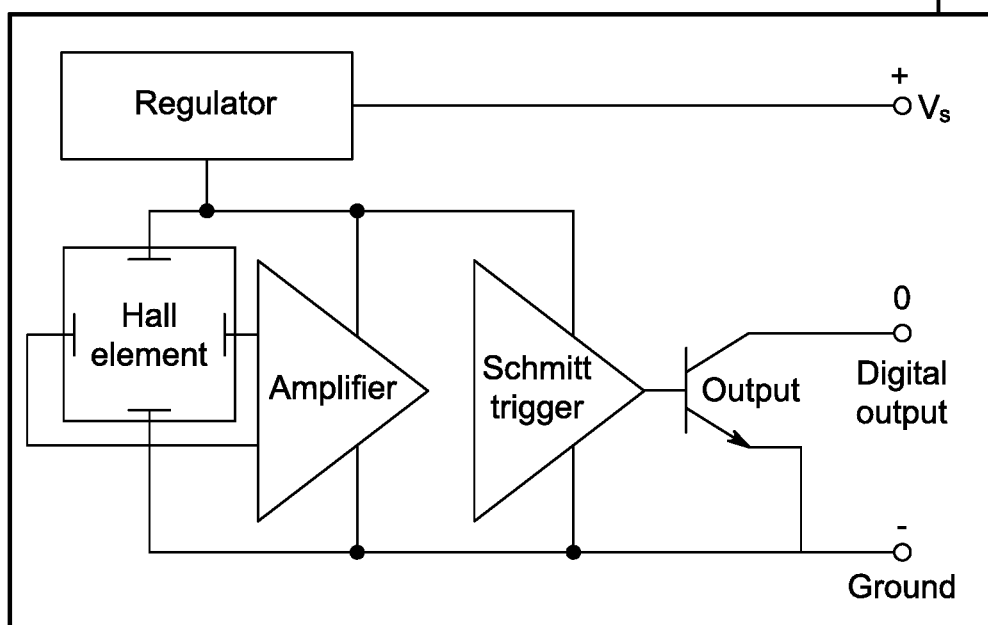
FIG. 15

COUCH TOP EXTENSION FOR RADIATION THERAPY AND IMAGING

TECHNICAL FIELD

This disclosure relates generally to radiation therapy and imaging. In particular, various embodiments of a couch top extension and a couch top for supporting patients during radiation therapy and/or imaging are described.

BACKGROUND

Various couches and couch tops for positioning and supporting patients are known in the art of radiation therapy and imaging. Accurate positioning and supporting of patients are crucial in both diagnostic imaging for determining the exact location of a target volume and related information and in treatment for precise delivery of high energy radiation to the target volume. Because the energies of radiation for diagnostic imaging (e.g. kV) and treatment (e.g. MV) are different, the couch tops used for supporting patients during imaging and treatment may be different. Radiation therapy has developed to treat various diseases in different body portions, including e.g. brain and neck cancers, breast cancers, and prostate cancers etc. Couch tops used in supporting patients for treatment of brain cancers may be quite different from those for treatment of prostate cancers. Further, the difference in patient's weight and size is also an important factor in designing or choosing a proper couch top for imaging and treatment delivery.

Therefore, there is a continuing need for improved couch tops for various clinical applications. It would be desirable to provide a system that allows safe and simple use of exchangeable couch top extensions to provide maximal flexibility. It would be desirable to provide a couch top that has an increased strength and stiffness and decreased radiation attenuation. It would be desirable to provide a coding system that allows identification of couch top extensions to ensure safety.

SUMMARY OF THE DISCLOSURE

An embodiment of a couch top extension comprises an extension board including a first section and a second section extending from the first section. The first section has a varying shape profile and the second section has a substantially uniform shape profile.

An embodiment of a couch top extension comprises an extension board comprising one or more identifiers capable of providing a detectable signal indicative of an identification of the extension board.

An embodiment of a couch top comprises an interface plate configured for attachment to a positioning device, and an extension board configured to removably couple with the interface plate. The extension board comprises a first section adjacent to the interface plate and a second section extending from the first section. The first section has a varying shape profile and the second section having a substantially uniform shape profile.

This Summary is provided to introduce selected embodiments in a simplified form and is not intended to identify key features or essential characteristics of the claimed subject matter, nor is it intended to be used as an aid in determining the scope of the claimed subject matter. The selected embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages of the disclosure will become better understood upon reading of the following detailed description and the appended claims in conjunction with the accompanying drawings, where:

FIG. 6A is a side view of the couch top extension shown in FIG. 5.

FIG. 6B is a top plan view of the couch top extension shown in FIG. 5.

FIG. 15 depicts an example sensor device and an electrical circuitry of the sensor device.

DETAILED DESCRIPTION OF EMBODIMENTS

Various embodiments of a couch top extension and a couch top useful to support patients for radiation therapy and/or imaging are described.

An example couch top extension includes a substantially uniform section configured to provide substantially constant radiation dose attenuation and homogenous build-up properties for clinical use, and a strengthened section configured to provide maximal strength and stiffness. The optimized shape of the couch top extension increases the maximal load capacity for supporting obese or heavy patients, decreases the minimal beam attenuation, and improves dose build-up effect beneficial for clinical applications.

An example couch top extension is encoded with identification information. The encoded identification information can be detected to allow verification if a correct couch top extension as planned is attached to the couch. The encoding system provides enhanced safety, allowing exchanging of couch top extensions even more feasible, thereby providing maximal versatility in choosing couch top extensions adapted for a particular clinical application in diagnostic imaging and treatment.

An example couch top extension includes a "core" construction comprising an outer "skin" or layer such as a carbon fiber or Kevlar fiber skin and a body of a low-density material sandwiched or enclosed within the outer skin. The core construction can be manufactured first and allows indexing rails to be attached to it thereafter. As such, the indexing rails can be constructed from a material that does not need to contribute to the couch top strength and stiffness. It also allows pre-fabrication of the indexing rails from a low-density material optimized for minimal attenuation of imaging or treatment beams. The core construction can be manufactured and configured to allow an attachment insert or frame to be secured thereto, thereby providing a safe and simple mechanism for attaching or dis-attaching the couch top extension to or from a couch or an interface plate affixed to a couch.

Figure 1:
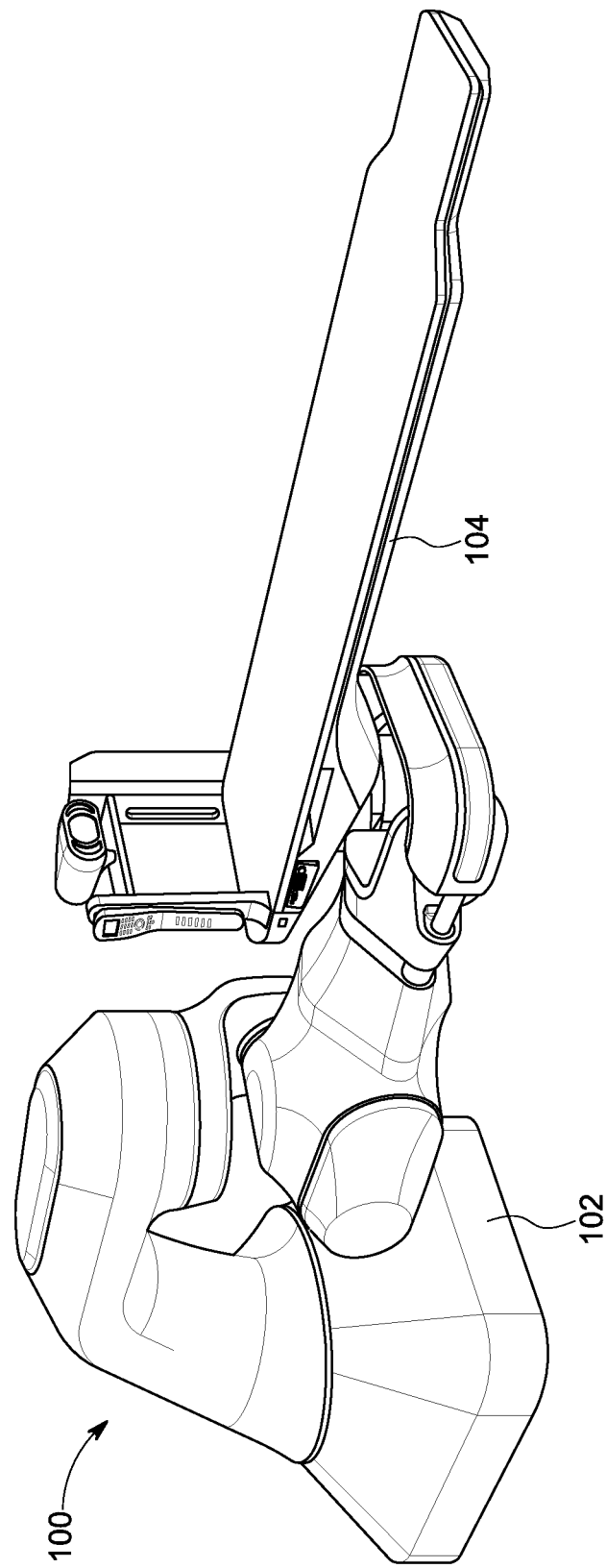
FIG. 1 depicts an example robotic couch and couch top according to embodiments of the disclosure.

With reference to FIGS. 1-18, various embodiments of a couch top and a couch top extension will now be described. FIG. 1 depicts an example positioning system 100 including a robotic couch 102 and a couch top 104 according to embodiments of the disclosure. It should be noted that while some embodiments are described in connection with a robotic couch, the couch top and couch top extension of the disclosure can be readily configured or modified for use with other forms of couches or positioning devices. Further, it should be noted that the couch top and couch top extension of the disclosure can be used with various imaging modalities including computed tomography (CT), cone beam computed tomography (CBCT), spiral CT, sliding CT, position-emission tomography (PET), fluoroscopy, radiography, ultrasound imaging, magnetic resonance imaging (MRI) etc., with various treatment systems using radiations such as x-rays, protons or heavy ions, electrons, etc., and in any other medical procedures or industrial applications.

As shown in FIG. 1, the positioning system 100 includes a couch or robotic couch 102 that can provide multiple degrees of freedom for the couch top 104 attached thereto. By way of example, the couch 102 may include one or more motion axes that allow the couch to freely move on the floor, thereby properly locating the couch top and thus a patient supported on the couch top relative to a radiation source. The couch 102 may include one or more motion axes that allow the couch top to translate vertically and/or horizontally. The couch 102 may also include one or more motion axes that allow the couch top to roll, pitch, or yaw. The couch top 104, as shown, may comprise a single piece fixedly attached to the couch 102. Alternatively, the couch top 104 may include multiple pieces or sections, for example, an interface plate fixedly attached to the couch and an exchangeable board coupled to the interface plate and extended to a treatment or imaging field when in use, as will be described in greater detail below. The couch top 104 may be optimized or configured for a clinical application. As shown in FIG. 1, the example couch top 104 comprises a head and shoulder configuration at the front-end configured for treatment or imaging of neck or head cancers. In some embodiments, the couch top 104 may be configured to allow a corner "filler" or add-on to be attached forming a generally rectangular standard board. The positioning system 100 shown in FIG. 1 provides full motion capability and great flexibility and versatility in positioning, loading, and unloading of patients.

Figure 2:
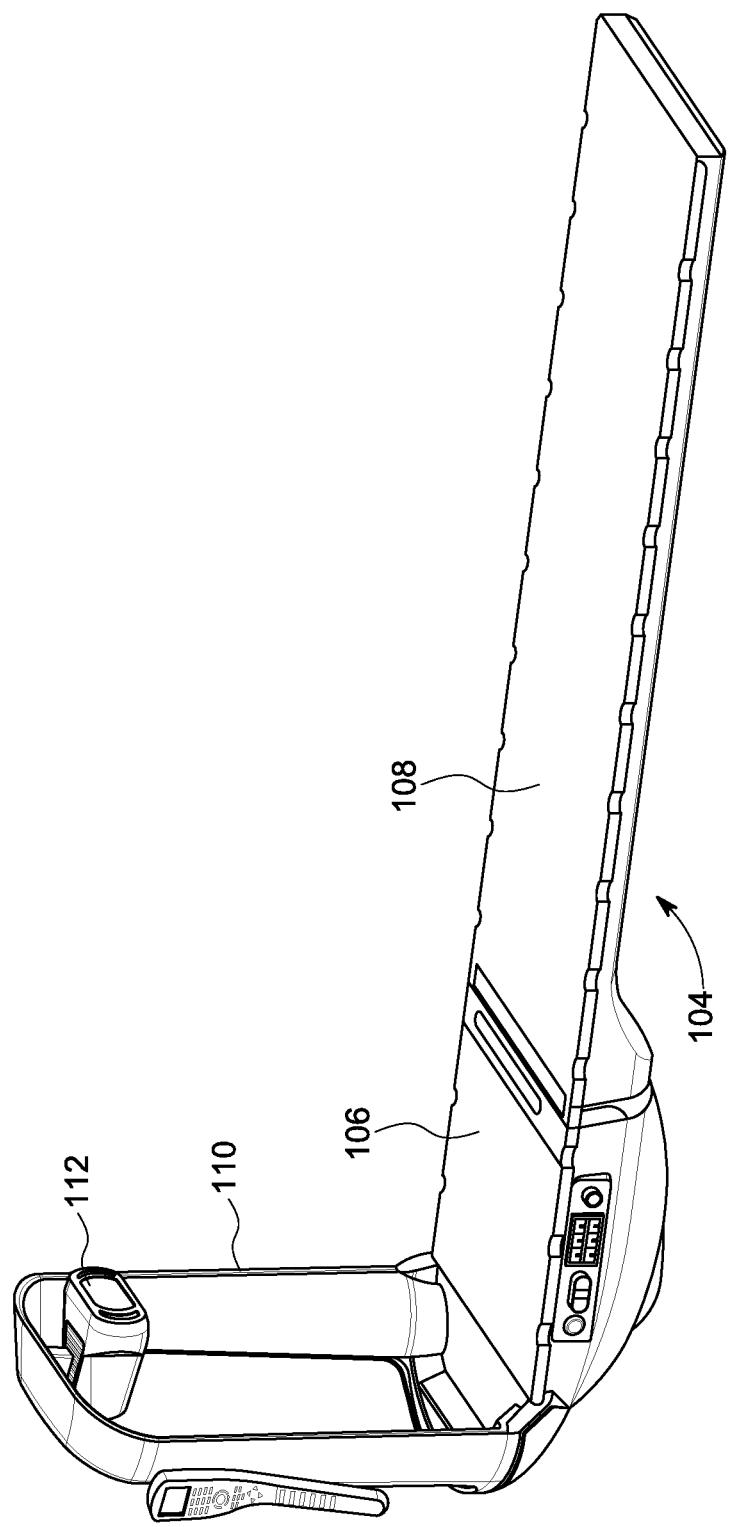
FIG. 2 depicts an example couch top according to embodiments of the disclosure.
Figure 3:
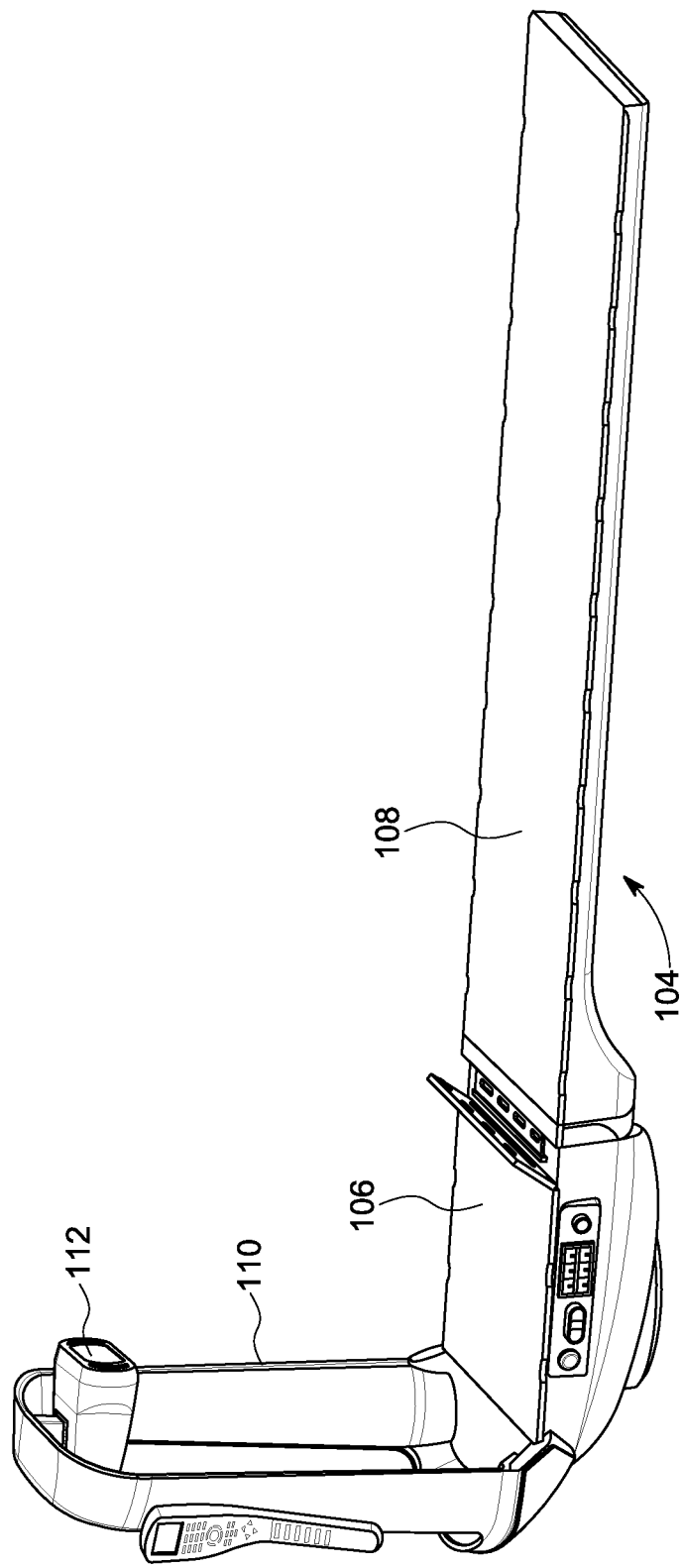
FIG. 3 depicts an example couch top showing a couch top extension attached to an interface plate according to embodiments of the disclosure.
Figure 4:
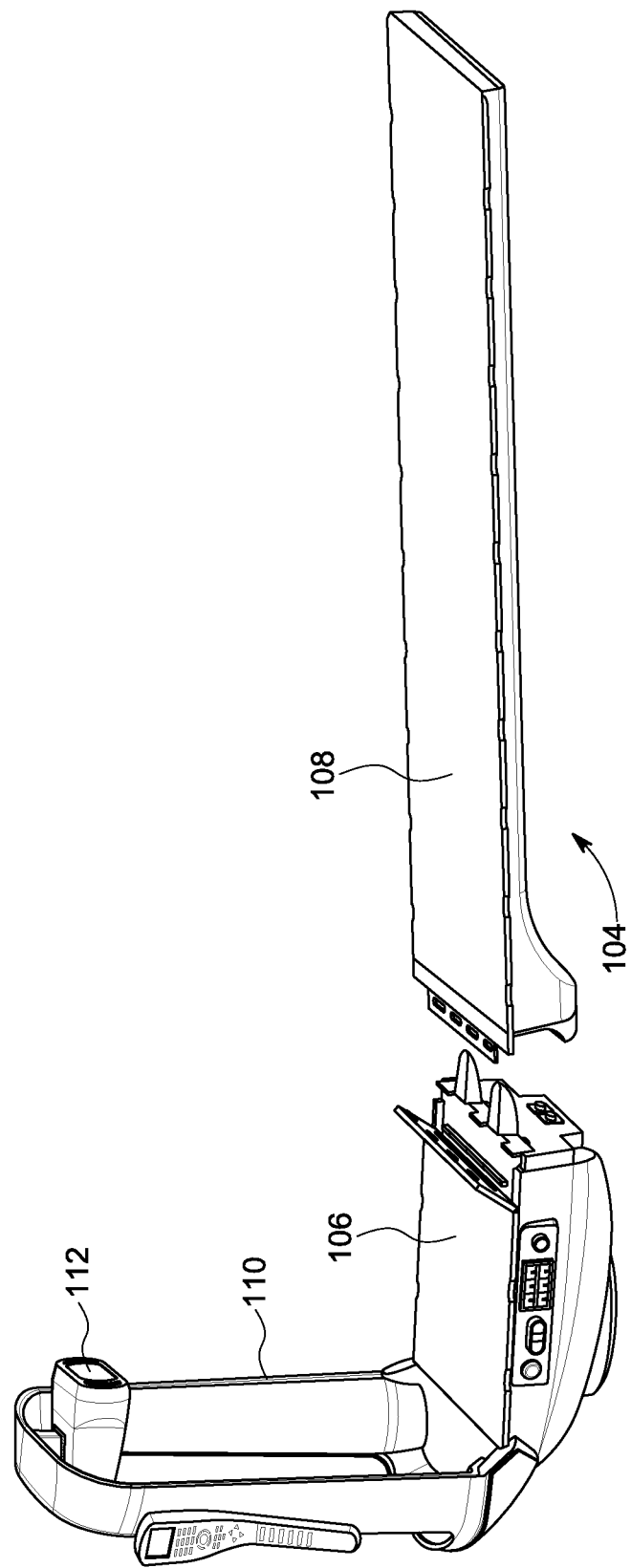
FIG. 4 depicts an example couch top showing a couch top extension attaching to or dis-attaching from an interface plate according to embodiments of the disclosure.

With reference to FIGS. 2-4, an example couch top 104 includes an interface plate 106 and a couch top extension 108 removably attached to the interface plate 106. The interface plate 106 may be fixedly attached to the couch 102 via any suitable means such as bolts, screws, or the like. The interface plate 106 provides a connection or interface such as a mechanical and electrical interface between the couch and the couch top extension. For example, the interface plate 106 may include an attachment mechanism for attaching or dis-attaching the couch top extension, and a locking mechanism for locking and releasing the couch top extension, as will be described in greater detail below. In some embodiments, the interface plate 106 may include a detection system for detecting the identification of a couch top extension, and/or other detection systems e.g. a load or momentum or force measuring system, as will be described in greater detail below. The interface plate 106 may also include various electrical components, connections, and/or circuitries for operation of the couch and couch top extension. A bridge or mount 110 may be coupled to the interface plate 106 to provide support for various accessories 112 such as beam gating system parts e.g. a camera or a visual coaching device. A couch-based imaging system, display, and control can also be mounted to the interface plate 106.

The couch top extension or extension board 108 is configured to removably couple with the interface plate 106. The couch top extension 108 allows the couch top 104 to have an extended section supported in a cantilevered manner (FIGS. 2-3). The extended section supported in a cantilevered manner can support at least a portion of a patient's body such as head, neck, arms, upper body, lower body, legs, or the entire patient's body for receiving treatment or imaging beams. The extended section supported in a cantilevered manner allows the body portion to be exposed in a free or open space, and thus allows a radiation source to direct multiple beams to the body portion at various angles. The extended section also provides for better physical and visual access to the body portion being treated or imaged. By way of example, the extended section supported in a cantilevered manner provides clearance, thereby allowing a source such as an accelerator or a treatment head of a radiation machine to deliver radiation to a treatment volume in a patient from below the extended section supporting the patient.

The couch top extension 108 includes an attachment mechanism, to be described in greater detail below, allowing the extension board to be attached to the interface plate 106 safely and easily, and dis-attached from the interface plate 106 quickly and simply (FIG. 4), as will be described further in greater detail below. The safe and simple attachment mechanism allows provision of a plurality of couch top extensions designed and constructed for various clinical uses and selecting one that is best suited for a particular patient for a particular clinical application.

Figure 5:
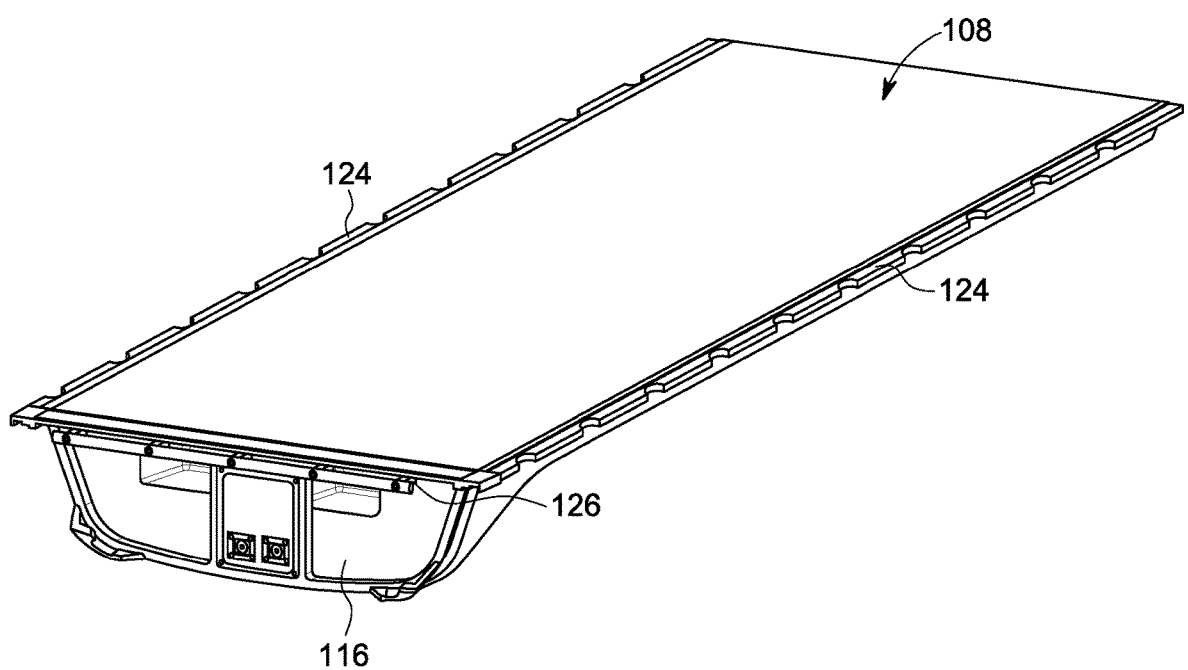
FIG. 5 depicts an example couch top extension according to embodiments of the disclosure.
Figure 6C:
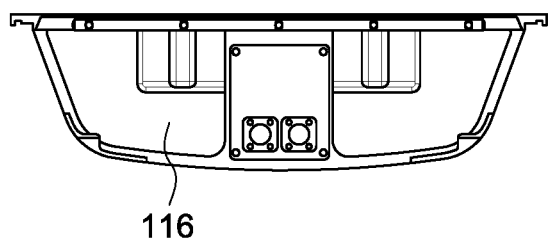
FIG. 6C is an end view of the couch top extension shown in FIG. 5.
Figure 6D:
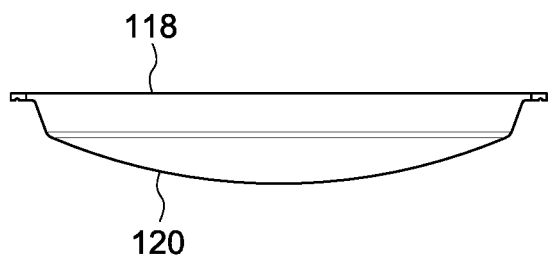
FIG. 6D is an end view of the couch top extension shown in FIG. 5.
Figure 6E:
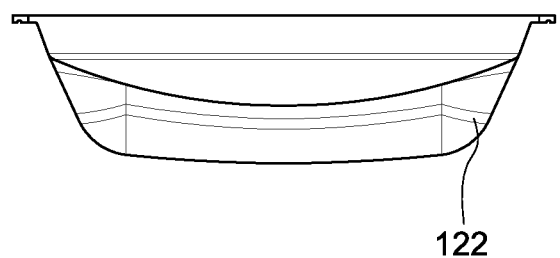
FIG. 6E is an end view of the couch top extension shown in FIG. 5.
Figure 6F:
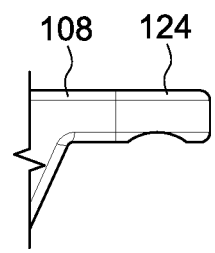
FIG. 6F is an enlarged view showing attachment of an indexing rail to the couch top extension shown in FIG. 5.
Figure 7:
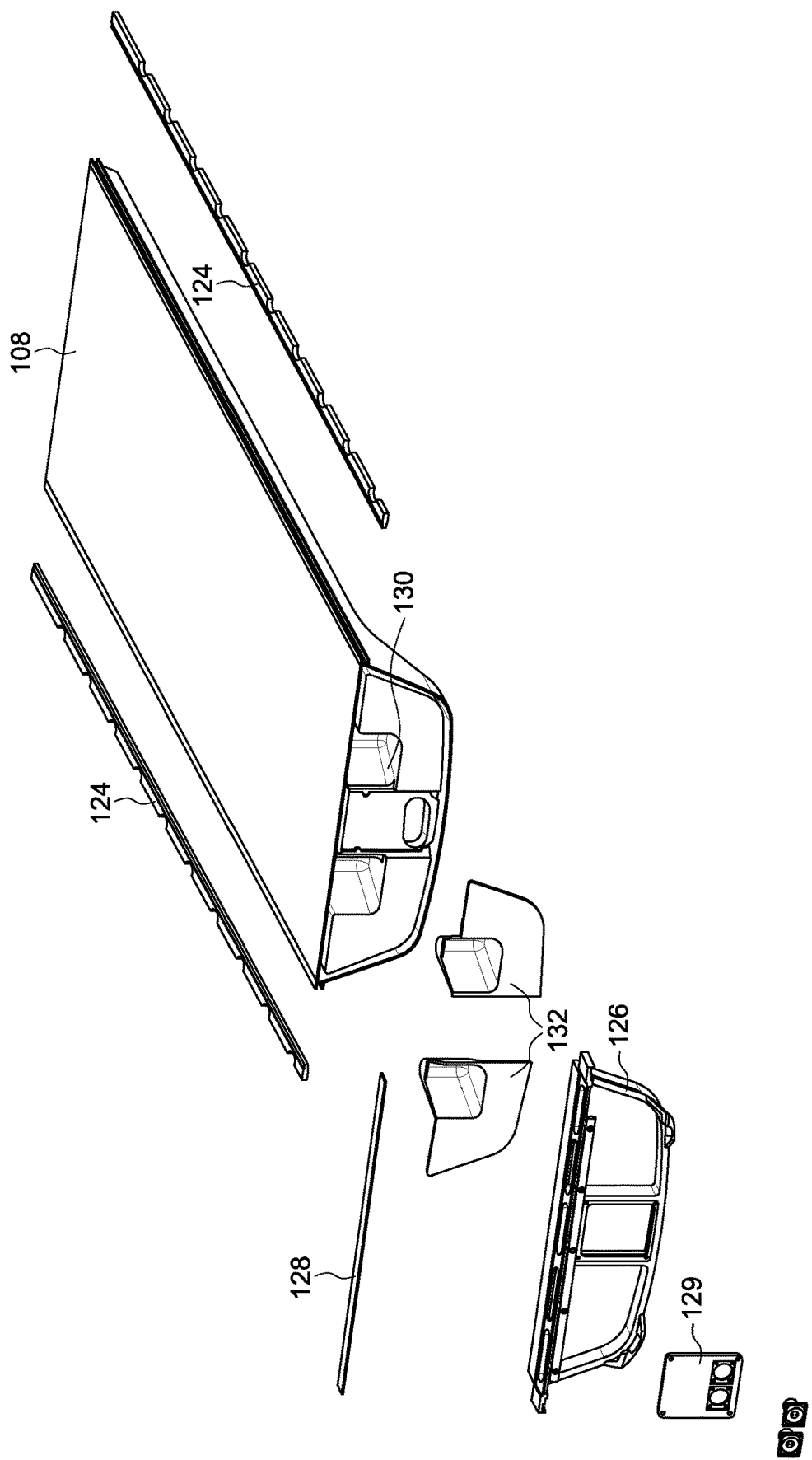
FIG. 7 is an exploded view of the couch top extension shown in FIG. 5.
Figure 8:
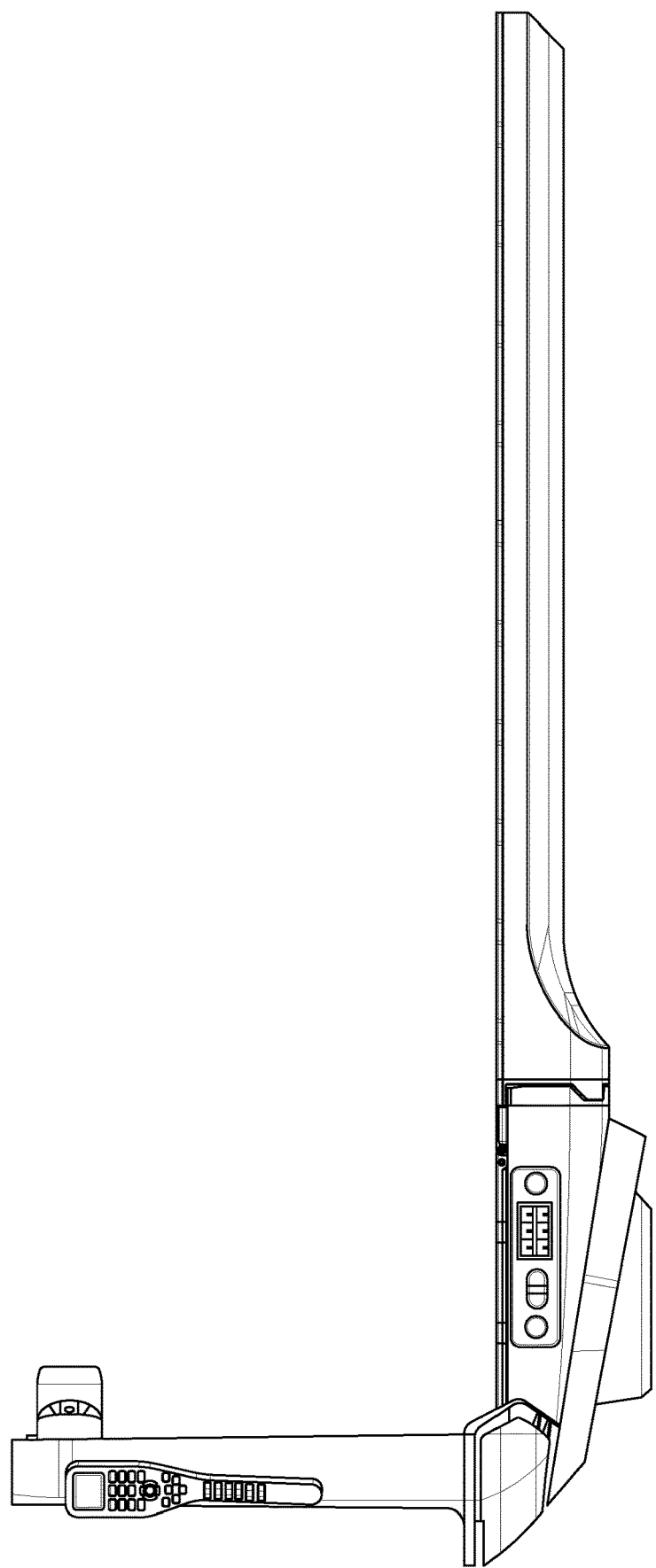
FIG. 8 is a side view of an example couch top including a couch top extension having an optimized shape according to embodiments of the disclosure.

FIG. 5 depicts a perspective view of an example couch top extension 108 according to embodiments of the disclosure. FIGS. 6A-6F depict side, top, and end views of the couch top extension 108 shown in FIG. 5. FIG. 7 is an exploded view of the couch top extension 108 shown in FIG. 5. FIG. 8 is a side view of the couch top extension 108 attached to an interface plate 106. As shown in FIG. 5-8, the couch top extension 108 of the disclosure includes a first section 113 and a second section 114 extending from the first section 113 (FIG. 6A). The first section 113 has an end or interface surface 116 to be coupled with the interface plate 106. The second section 114 extends into the treatment or imaging field when in use, allowing a body portion supported by the couch top to be exposed to radiation.

In accordance with embodiments of the disclosure, the second section 114 of the couch top extension 108 has a substantially uniform shape profile. As used herein, the term "substantially uniform shape profile" means that the shape or geometry is reasonably same and is intended to take into consideration small changes in geometry that may occur in manufacturing. A uniform shape profile can provide a constant radiation dose attenuation and homogenous build-up properties, which is desirable for clinical use. As better shown in FIGS. 6A and 6D, the second section 114 may have a flat top surface 118 and a rounded or curve bottom surface 120. The flat top surface 118 and curve bottom surface 120 may be substantially uniform across the entire second section. Other uniform shape profiles for the second section 114 are possible, including but not limited to, a flat top surface and a flat bottom surface, a flat top surface and a curve bottom surface having e.g. a partial-circle cross-section profile, a flat top surface and a bottom surface having an approximate trapezoidal cross-section profile, a top surface having a concave or curve portion and a flat bottom surface, a top surface having a concave or curve portion and a rounded or curve bottom surface having e.g. a partial-circle cross-section profile, a top surface having a concave or curve portion and a bottom surface having an approximate trapezoidal cross-section profile, etc. Indeed, the second section 114 having a uniform or substantially uniform shape profile can have any suitable combination of a top surface and a bottom surface each having a configuration optimized for providing a constant radiation dose attenuation and homogenous build-up properties suitable for a particular imaging and/or treatment application. It should be noted that each of the top and bottom surfaces can consist of a single continuous surface or of multiple surface portions combined. The shape profile of the second section 114 can be optimized to decrease the minimal beam attenuation beneficial for clinical applications.

The first section 113 of the couch top extension 108 may have a varying shape profile. In accordance with embodiments of the disclosure, the first section 113 does not extend to the treatment or imaging field when in use. As such, the first section 113 can be configured or constructed to provide strength and stiffness for the couch top extension 108. FIGS. 6A and 6E better show a varying shape profile of the first section 113. By way example, the first section 113 may have an increasing thickness towards the end or interface surface 116 that would couple the couch top extension 108 with the interface plate 106. As another example, the cross-sections of the first section 113 may have a generally trapezoidal shape 122 (FIG. 6E), and the size or area of the trapezoidal shape 122 of the cross-sections increases towards to the end surface 116. Other suitable shape profiles of the first section 113 are possible and contemplated by the inventors. For example, the cross-sections of the first section 113 may have a shape of a partial circle or arc, and the size or area of the partial circles increases towards to the end surface that faces the interface plate. The increased thickness or area in cross-section towards the end surface allows more materials to be used to construct the first section, providing a strengthened area for the couch top extension. Further, because the first section 113 does not need to extend to the treatment or imaging field when in use, a material of relatively high-density, or a material different from a low density material as used for the second section, can be used to construct the first section 113, providing a reinforced area for the couch top extension 108. As such, the first section 113 can be optimized to increase the maximal load capacity for supporting heavy patients.

The first and second sections 11, 114 of the extension board 108 can be integrally constructed, e.g. as a single or modular unit. The integral extension board 108 may have a sandwich structure comprising an outer "skin" or layer and a body of a low-density material sandwiched between or enclosed within the outer skin or layer, forming a "core" construction of the extension board. The outer skin can be constructed from a lightweight yet high-strength material such as carbon fiber, Kevlar fiber, or other synthetic composites. Examples of low-density material sandwiched between the outer skin include radiation tolerant hard foam or closed-cell foam such as ROHACELL® hard foam commercially available from Evonik of Essen, Germany. The sandwich structure of the core construction provides a strong yet light extension board to facilitate attaching, dis-attaching, or exchanging of extension boards. In some embodiments of the disclosure, the first section 113 of the extension board 108, where no treatment or imaging beam goes through it when in use, can be constructed from any other suitable materials to strengthen or reinforce the extension board. For example, carbon fiber, an injection molded material, metal, or high-density foam can be used for the first section of the core construction.

The core construction or extension board 108 can be designed or optimized based on clinical applications. Because the extension board 108 can be exchanged, the core construction 108 can be optimized to provide specific radiation attenuation and/or dose build-up properties for imaging or treatment respectively, or for both treatment and imaging. The core construction or extension board 108 may be optimized based on patient's sizes and/or weights to provide an optimal combination of load capacity, stiffness, and dosimetric effect. The core construction or extension board 108 may be configured for lying-down treatment (prone or supine), sit-up treatment or whole-body treatment. The core construction or extension board 108 may be shaped or configured for treatment and/or imaging of a particular disease such as brain cancer, neck cancers, breast cancers, lung cancers, prostate cancers, and so on. Indeed, various options may be provided in manufacturing the core construction or extension board 108 according to the principle of the disclosure.

In some embodiments, the core construction or extension board 108 may be configured to allow an additional insert to be attached to further expand the couch top system. For example, the top surface of the core construction may be generally in a rectangular shape and the core construction may be further configured to allow an "add-on" having a head and shoulder shape to be attached for treating or imaging head or neck cancer. In some embodiments, the interconnection of an additional insert to the core construction may be motorized to allow angle adjustment.

In some embodiments, the core construction 108 can be manufactured "non-conductive" by using a non-conductive material such as Kevlar fiber skin. A non-conductive core construction would be desirable where a transponder tracking system is used in a clinical application to avoid effects or interference of a conductive couch support. Calypso Beacon® is an example transponder tracking system commercially available from Varian Medical Systems, Inc. of Palo Alto, Calif., U.S.A. In some embodiments, the core construction may include an antenna panel such as a thin metal wire tag to facilitate reception of signals from a transponder of e.g. a Calypso Beacon® tracking system. The electrical connections for the input and output of the antenna panel can be disposed in the interface plate and the first section of the core construction or outside the treatment or imaging field when in use. The antenna panel can be placed at various positions on or in the core construction and its position can be identified via the electrical connections. In some embodiments, the antenna may be removed when it is not used in a clinical application.

In some embodiments, various sensing devices may be built in the core construction 108 to extend various functionalities of the couch top. By way example, one or more capacitive sensors may be included in the core construction 108 to allow detection of motion of the patient relative to the couch top. As another example, one or more load cells or sensors may be included in the core construction 108 to allow detection of the weight of the patient on the couch top. The motion or load detection mechanisms and sensing devices may be disposed in the interface plate 106. In some embodiments, one or more fiducial markers may be embedded in the core construction 108 to allow imaging-based checking of the position of the couch top.

According to embodiments of the disclosure, indexing rails may be attached to the core construction 108, providing a new indexing system for a couch top.

With reference to FIG. 7, in some embodiments, indexing rails 124 may be attached to the extension board 108 after a core construction is manufactured. As such, the indexing rails 124 can be pre-fabricated or purchased from any manufacturer. The indexing rails 124 may be constructed from a material that does not need to contribute to the couch top strength and stiffness. Alternatively, the indexing rails 124 can be constructed from a material that contributes couch top strength and stiffness. In some embodiments, the indexing rails 124 are pre-fabricated from a low-density material optimized for minimal imaging and treatment beam attenuation. Example materials that can be used for constructing indexing rails 124 include but are not limited to polyurethanes such as BAYDUR® commercially available from Covestro AG of Germany, low-density epoxy polymers, and other suitable materials. The indexing rails 124 can be bonded to the lateral sides of the core construction 108 using a suitable glue (FIG. 6F). Alternatively, the lateral sides of the core construction 108 can be configured to allow the indexing rails 124 to attach to the extension board by friction or interference. The indexing features may be in the form of notches or have mounting features arranged in a predetermined interval, to allow accessories to be secured to the extension board. The accessories may be restraining or immobilization devices or supporting devices such as headset, breast board, SRS overlay board etc. The locations of the accessories can be indexed by the indexing system 124, providing an efficient and reproducible patient support. FIG. 5 is a perspective assembled view showing the indexing rails 124 being attached to the lateral sides of the core construction 108.

According to embodiments of the disclosure, an attachment frame may be inserted to the core construction, providing a safe and simple mechanism for attaching the extension board to an interface plate and yet a stiff support allowing the couch top to rotate in various degrees of motions with reduced displacement.

Figure 9:
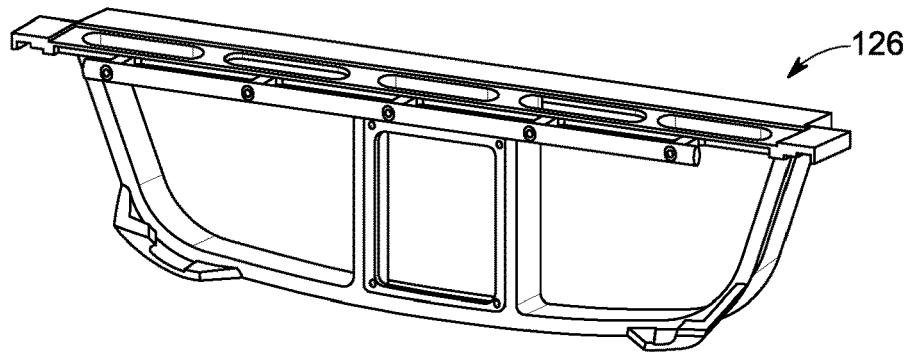
FIG. 9 depicts an example attachment frame according to embodiments of the disclosure.
Figure 10:
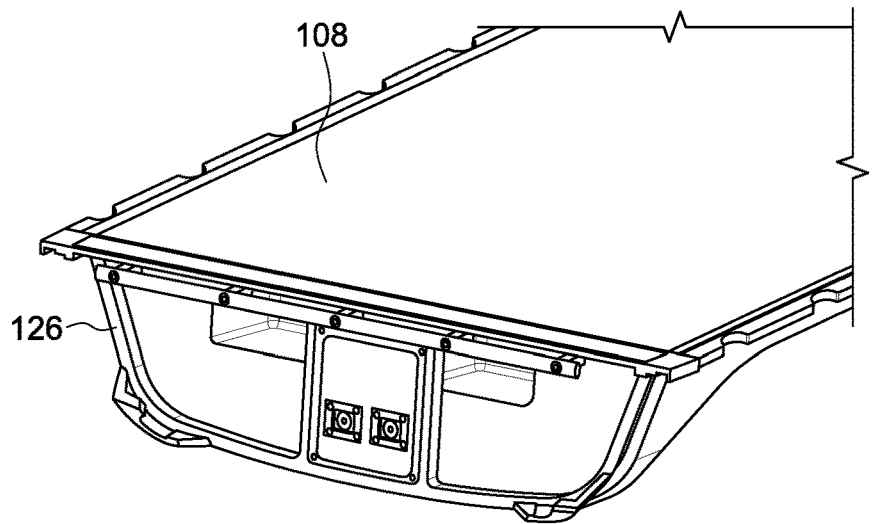
FIG. 10 depicts the attachment frame shown in FIG. 9 laminated or glued to a couch top extension according to embodiments of the disclosure.
Figure 11:
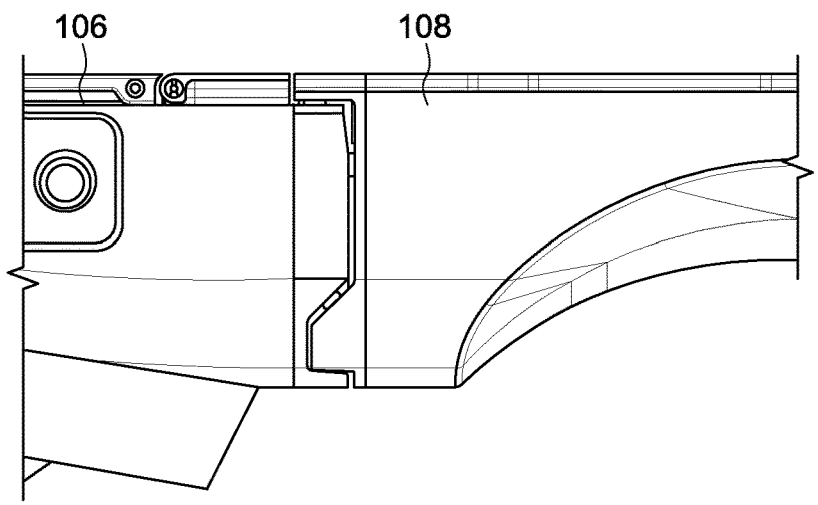
FIG. 11 depicts attachment of an example couch top extension to an interface plate using the attachment frame shown in FIG. 9 according to embodiments of the disclosure.

With reference to FIG. 7, an attachment frame 126 may be incorporated to the end portion of the extension board 108. As shown, an example attachment frame 126 may include a cross bar configured to hook or engage one or more complementary hook features in the interface plate 106. The attachment frame 126 may be constructed from a metal such as aluminum, stainless steel or alloys that provides strength and stiffness. In some embodiments, the attachment frame 126 is constructed from aluminum providing both strength, stiffness and low weight for the extension board. The attachment frame 126 may have a shape generally the same as or similar to the shape of the end surface of the extension board 108, allowing the attachment frame to fit in the end portion of the extension board. The attachment frame 126 may be inserted into and bonded to the end portion of the extension board 108 using a suitable glue. Other means such as screws or the like can be used to secure the attachment frame to the end portion of the extension board. Reference 128 indicates a frame insert cover. In some embodiments, the end portion of the extension board 108 may have one or more recesses 130 for receiving one or more complementary projections in the interface plate. The one or more recesses and one or more complementary projections allow alignment of the extension board 108 with the interface plate 106 and provide stiff and strong support for the couch top. Reference 132 indicates front recess covers. FIG. 9 depicts an example attachment frame 126 with greater clarity. FIG. 10 depicts the attachment frame 126 being laminated or glued to the end portion of the couch top extension 108. FIG. 11 depicts attachment of the extension board 108 to the interface plate 106 using the attachment frame 126.

Figure 12A:
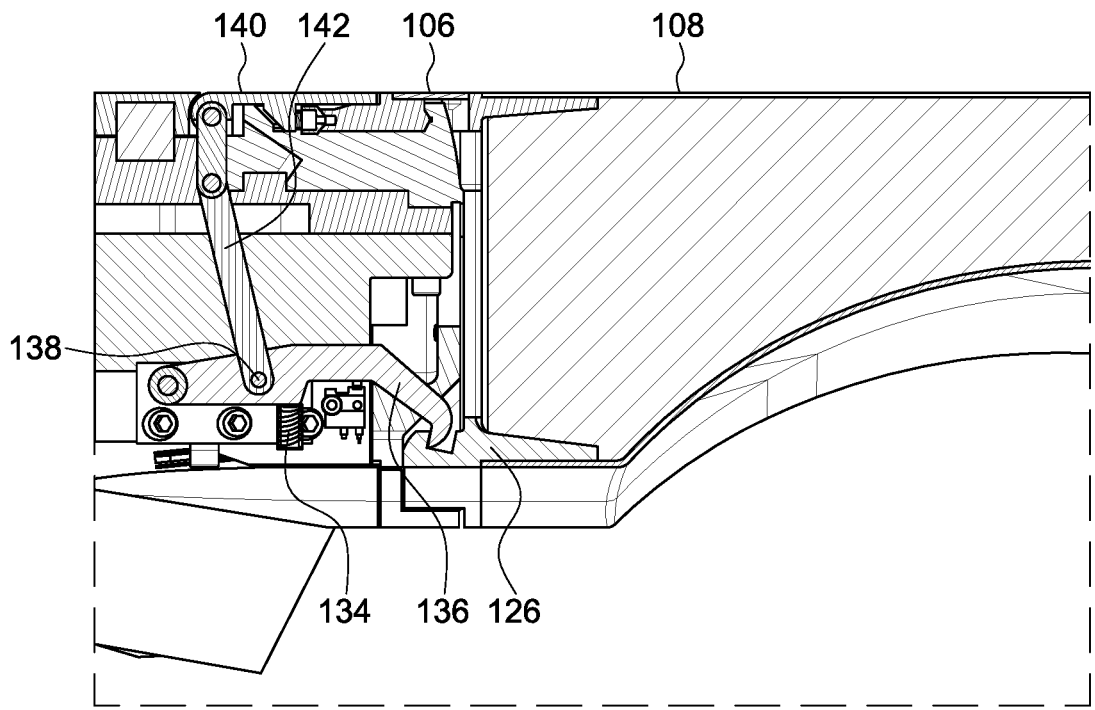
FIG. 12A depicts an example locking mechanism in a locked state securing a couch top extension to an interface plate according to embodiments of the disclosure.
Figure 12B:
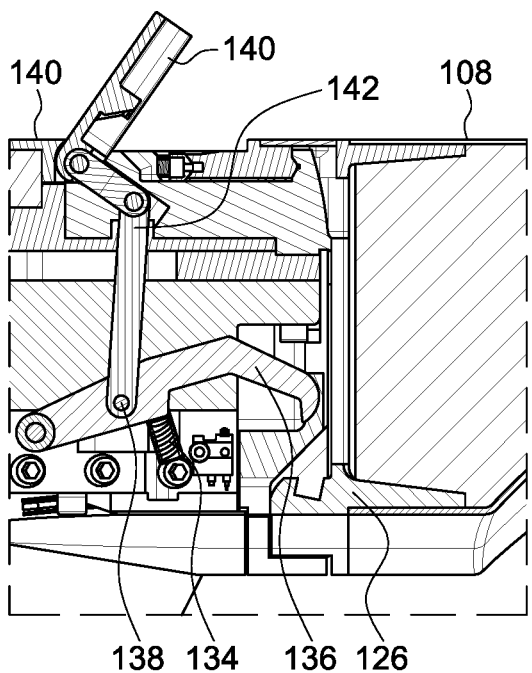
FIG. 12B depicts the example locking mechanism shown in FIG. 12A in an unlocked state.

With reference to FIGS. 12A-12B, according to embodiments of the disclosure, a locking mechanism is provided to lock the extension board 108 once attached to the interface plate 106 to ensure safety. As shown, an example locking mechanism may include a tension spring 134 that couples a locking lever 136 to the interfacing plate via a pin member 138. The locking lever 136 has a hook feature at an end configured to engage with a hook feature in the attachment frame 126 in the extension board 108. The tension spring 134 has a rest or natural state, as shown in FIG. 12A, wherein the locking lever 136 engages with the attachment frame 126 locking the extension board 108 to the interfacing plate 106, and a stretched state, as shown in FIG. 12B, wherein the locking lever 136 disengages from the attachment frame 126 unlocking the extension board 126. The locking mechanism may include a handle bar 140, which couples with the tension spring 134 via one or more lever members 142 and pin member 138. The handle bar 140 allows a user to stretch the tension spring 134 by lifting the handle bar 140, thereby disengaging the locking lever 136 from the attachment frame 126. Release of the handle bar 140 would allow the tension spring 134 to return its original natural state. In some embodiments, the locking mechanism can be released by a release mechanism (not shown) which may be triggered by inserting the couch top extension 108.

It should be noted that the attachment and locking mechanisms shown in FIGS. 9-12 are provided for illustration purpose. The exchangeable couch top extension 108 of the disclosure can be attached to and dis-attached from the interface plate 106 using any other suitable mechanisms, and the claimed invention is not so limited.

Figure 18A:
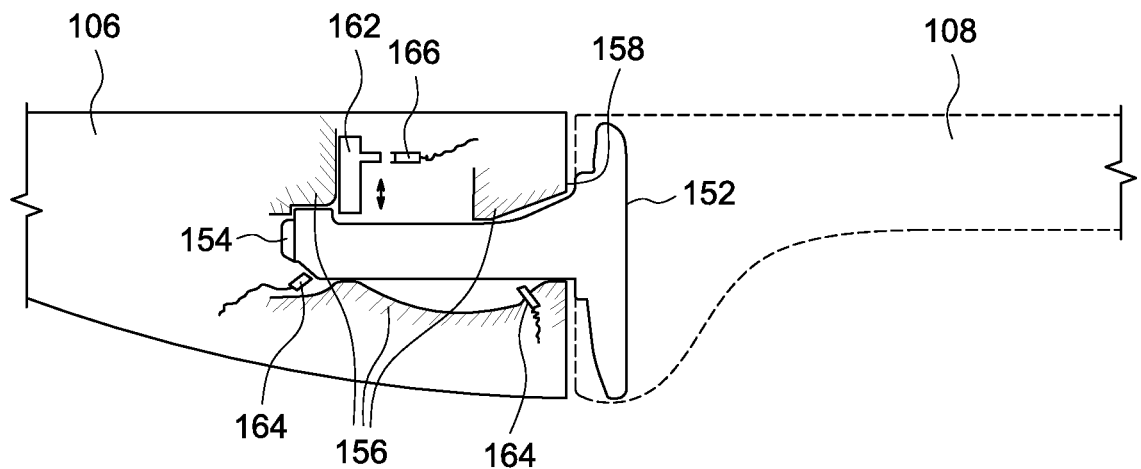
FIGS. 18A-18G depict an interface mechanism according to alternative embodiments of the disclosure.
Figure 18B:
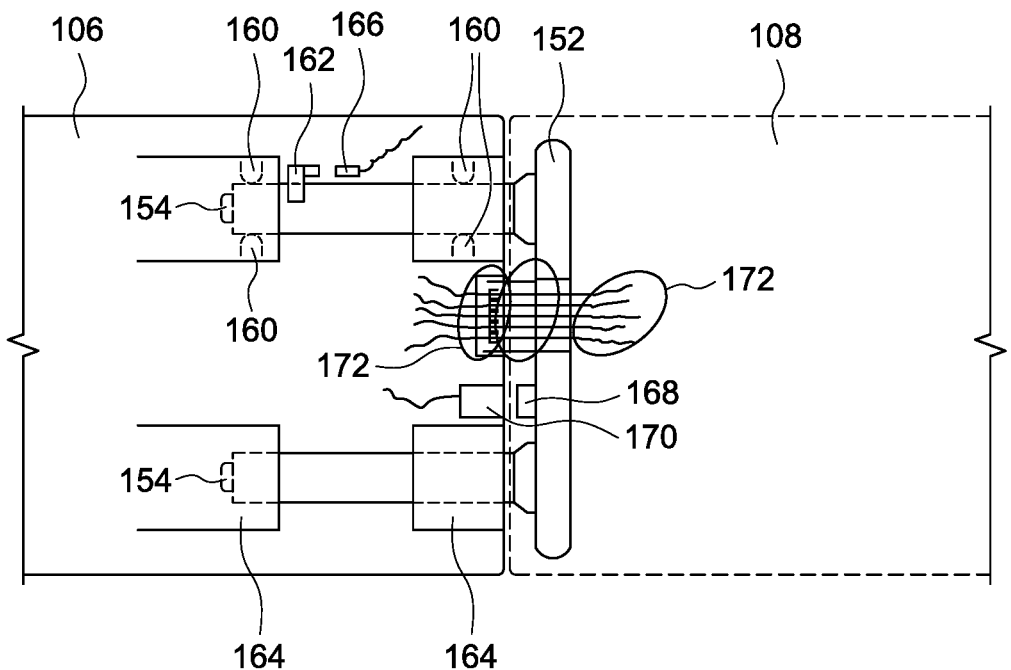

With reference to FIGS. 18A-18G, an alternative attachment and locking mechanism according to embodiments of the disclosure is provided. As shown in FIGS. 18A-18B, one or more interface pieces or bars 152 may be attached to the end portion of extension board 108. The interface piece 152 may be constructed from a metal and attached to the extension board 108 by bonding or other suitable means. The interface piece 152 may include an extended bar and a hook feature at the end portion of the bar for engaging with a locking mechanism 162 inside the interface plate 106. Protection bumper 154 may be attached to the end of the extended bar of the interface piece 152 to reduce hard impact to other parts inside the interface plate. The interface plate 106 includes carrying structures 156 inside a cavity in the interface plate. The cavity has an opening 158 sized and shaped to receive the interface piece 152. Guide members 160 may be provided inside the cavity to guide the interface piece 152 to a locking position or "in-position." A locking lever 162 may engage the hook feature of the interface piece 152 once the interface piece 152 is in the locking position. Sensors 164 may be provided inside the interface plate 106 providing signals indicating the position the interface piece 152, such as at an intermediate position, a locking position or in-position, and so on. A locking sensor 166 provides a signal indicating the locked or unlocked state of the locking lever 162, adding additional safety to the mechanism. Similar to the embodiments shown in FIGS. 9-12, a coding system may be provided including an extension board identifier 168 on the extension board 108 and an identifier reader 170 on the interface plate 106. Electrical interface 172 between the extension board 108 and the interface plate 106 is provided via e.g. connection plug and socket or other suitable mean.

Figure 18C:
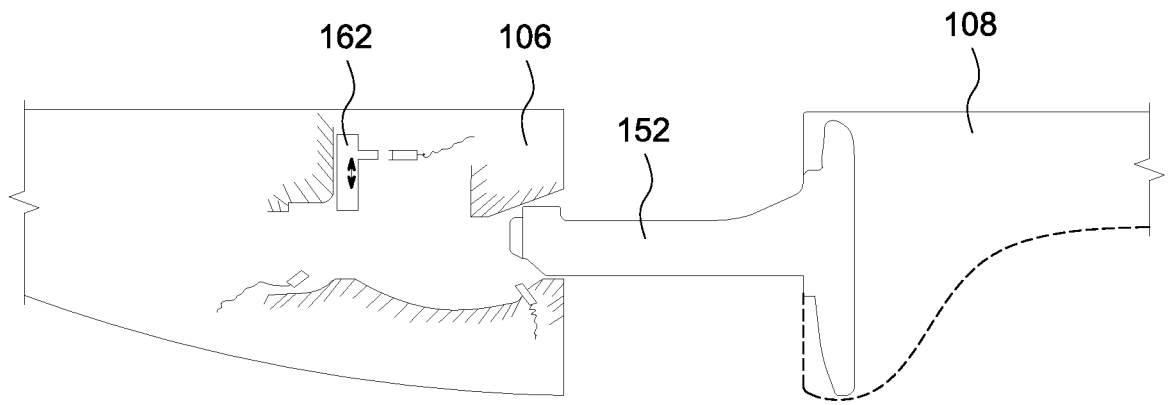
Figure 18D:
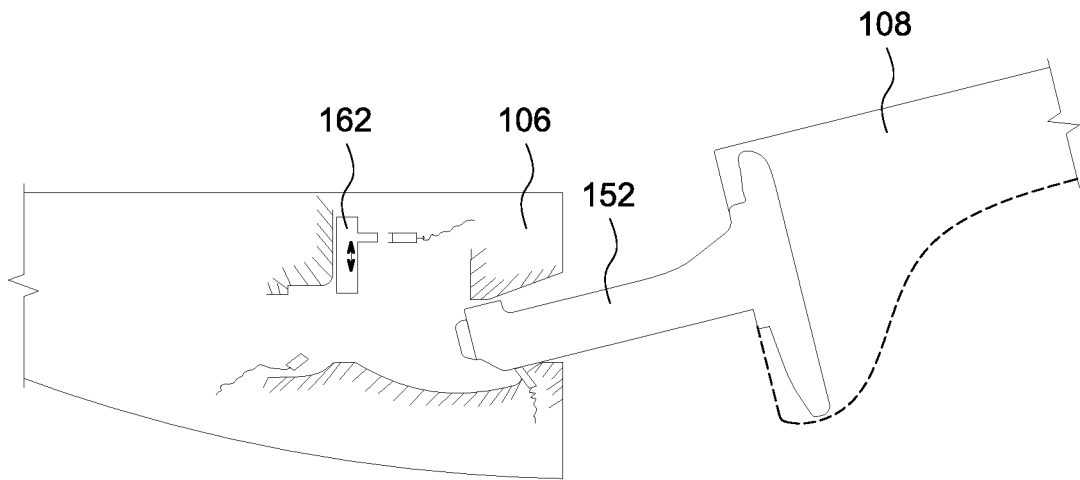
Figure 18E:
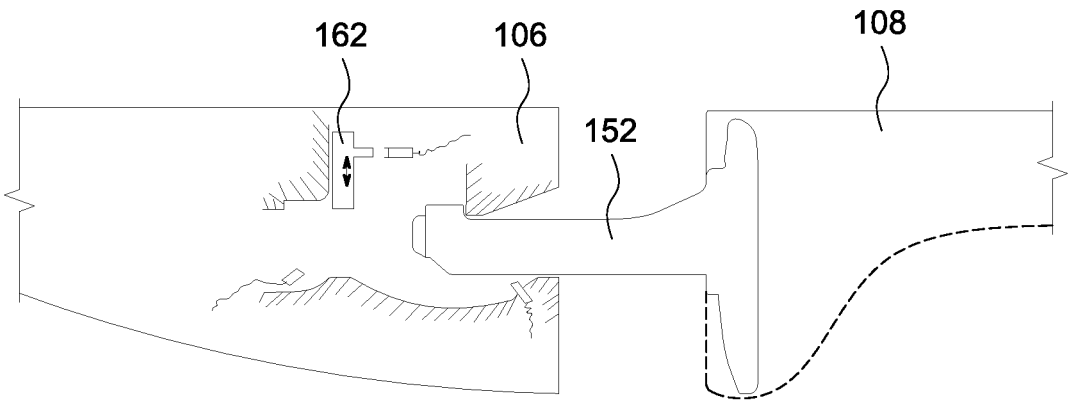
Figure 18F:
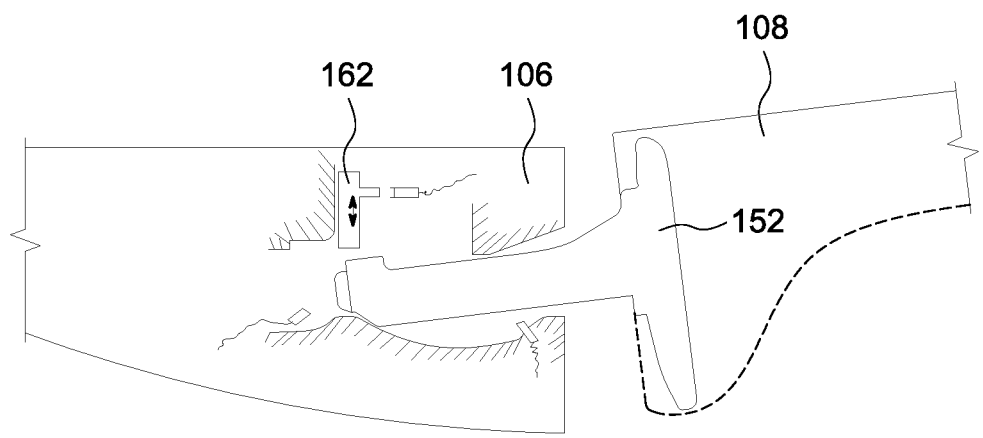
Figure 18G:
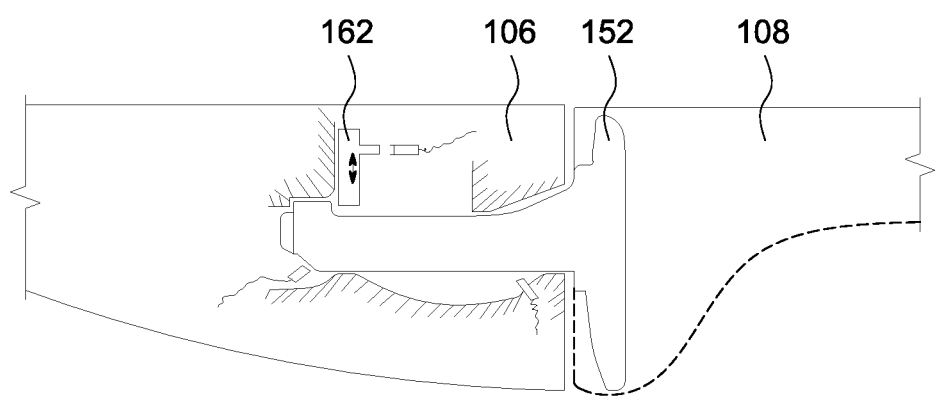

As demonstrated in FIGS. 18C-18G, the mechanism allows the extension board 108 to be attached and locked to the interface plate 106 easily and safely. The configuration of the cavity opening in the interface plate 106 allows the extended bar 152 on the extension board 108 to easily find the attachment, as indicated in FIGS. 18C and 18D. Advantageously, the carrying structures in the interface plate 106 allows the extension board 108 to be in a safe intermediate position, as indicated in FIG. 18E, reducing or eliminating the need to keep holding the extension board 108 during the entire attaching or dis-attaching process. From the intermediate position shown in FIG. 18E, the extension board 108 can be pushed and guided further to the "in-position," and then locked by a locking lever 162, as indicated in FIGS. 18F and 18G. To unlock and dis-attach the extension board 108, the steps illustrated in FIGS. 18C-18G are reversed, allowing the extension board 108 to be released and lifted from the interface plate 106.

Figure 13:
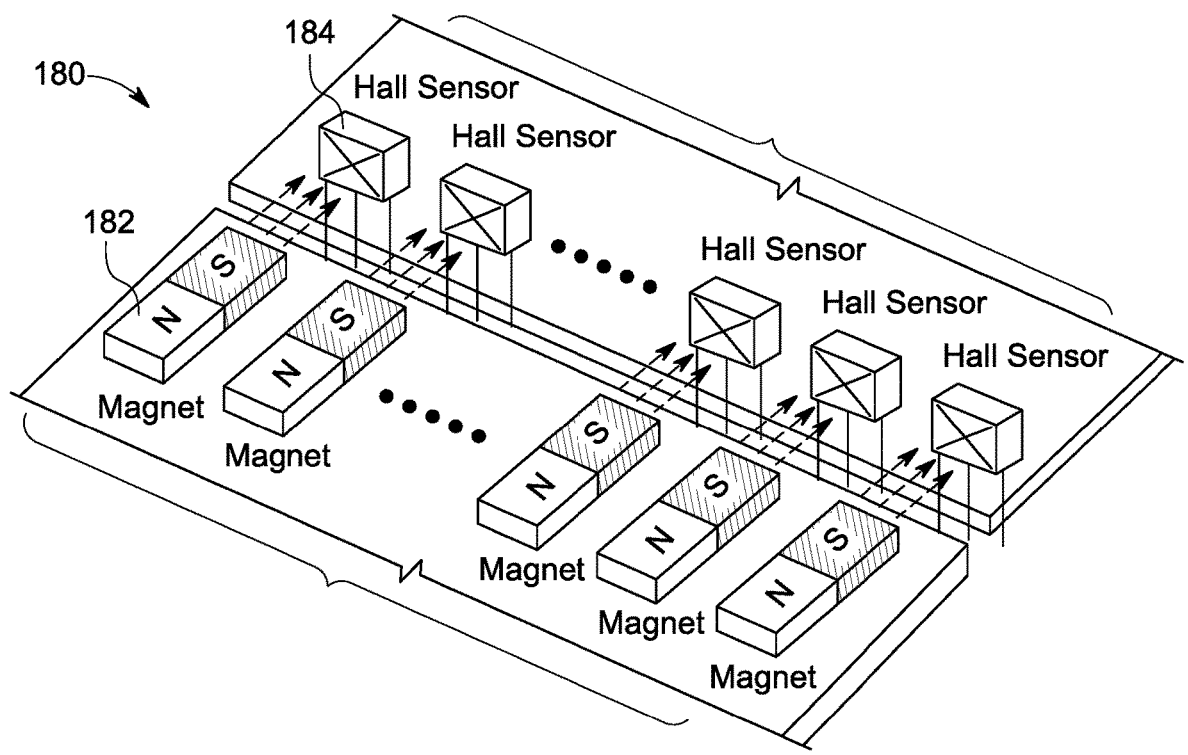
FIG. 13 depicts an example coding system according to embodiments of the disclosure.
Figure 14:
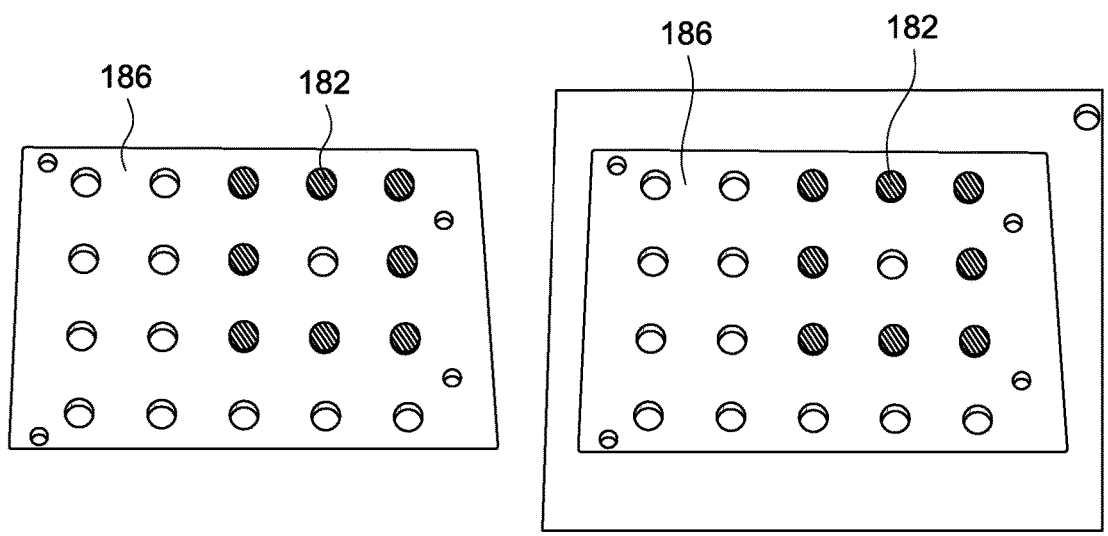
FIG. 14 depicts an example array of magnets according to embodiments of the disclosure.

With reference now to FIGS. 13-15, according to embodiments of the disclosure, a coding system 180 is provided to allow identification information to be encoded to a couch top extension and detected. The coding system 180 allows a control system such as a treatment delivery system to verify if a correct couch top extension as planned in a patient treatment plan is attached to the couch. Upon verification that a correct couch top extension is attached, the control or treatment delivery system can adapt its software collision prevention model based on the actually attached couch extension board. If it is verified that an incorrect couch top extension is attached, a warning signal or interlock may be generated and sent to the treatment delivery system. The identification information that can be encoded to the extension board includes but is not limited to extension board part ID, serial number, version, product information, clinical application information, manufacturing information, and so on.

The identification information may be encoded by one or more identifiers 182 which are capable of providing a signal indicative of the identification of the extension board. The signal provided by the one or more identifiers 182 can be detected by one or more detectors 184. The one or more identifiers 182 may be placed in or on the extension board 108 such as the first section of the extension board. The one or more detectors 184 may be placed in or on the interface plate 106 or the couch to which the interface plate is attached. By way of example, the one or more identifiers 182 may include a magnetic element producing an electromagnetic field signal which can be detected by a sensing element 184. As another example, the one or more identifiers may include a passive or active transmitter providing an output signal that can be detected by a receiver or sensor such as an ultrasound sensor, capacitive sensor, or a camera e.g. infrared camera. As another example, the one or more identifiers may include a radio frequency identification (RFID) tag which can be detected by an RFID reader. As a further example, the one or more identifiers may include a fiducial marker which can be detected by an imaging system. According to embodiments of the disclosure, the one or more identifiers 182 may act or function as a binary data record and the one or more detectors 184 may act or function as a binary data reader.

FIG. 13 depicts an example coding system 180 according to embodiments of the disclosure. The example coding system 180 includes an array of magnetic elements 182 and an array of sensing elements 184. The identification information of an extension board can be encoded by an array of magnetic elements arranged in a predetermined pattern, and detected by an array of sensing elements. As shown in FIG. 14, a template or plate 186 provided with a plurality of holes in rows and columns can be used to arrange an array of magnetic elements 182 in a particular pattern (code for extension board ID). The plate 186 with an array of magnetic elements 182 in a pattern can be placed on the extension board 108 e.g. on an end portion of the extension board. In FIG. 7, a center cover 129 would cover a plate of an array of magnets on the end portion of the extension board 108. The pattern of the array of magnetic elements or the identification code can be detected by an array of sensing elements disposed e.g. on the end portion of the interface plate 106. The ID information of an extension board 108 can be then read out, and provided to a control or treatment delivery system for verification. FIG. 14 shows two example plates each carrying a different number of magnetics arranged in a predetermined pattern. Each of the plates provides unique identification information to an extension board, which can be detected, read out, and provided to a control or treatment delivery system.

Figure 16:
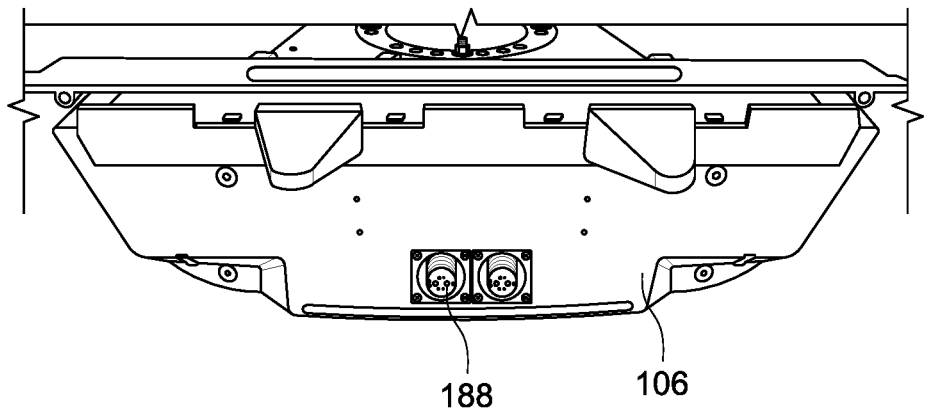
FIG. 16 depicts an example electrical interface on an interface plate according to embodiments of the disclosure.
Figure 17:
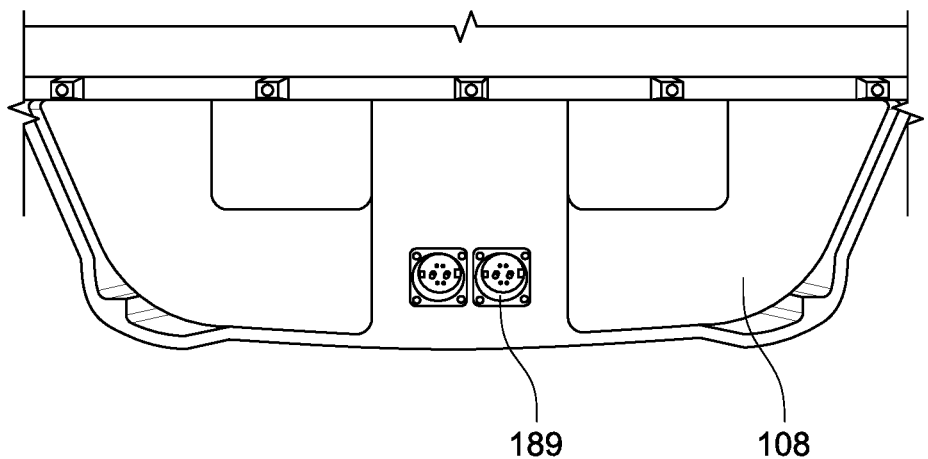
FIG. 17 depicts an example electrical interface on a couch top extension according to embodiments of the disclosure.

An example magnetic element 182 may include a permanent magnet comprising a ferromagnetic material such as iron, nickel or cobalt or a combination thereof. An example magnetic element 182 may also include an electromagnet comprising a coil of wire wound around a core of ferromagnetic material. The coil of wire acts as a magnet when a current pass through it and stops being a magnet when the current stops. The sensing element 184 can be any suitable sensing element capable of detecting a magnetic field signal. An example sensing element includes a Hall effect sensor or H-sensor device or a reed contact switch. FIG. 15 depicts an example H-sensor device 184 and an electrical circuitry diagram of the H-sensor. H-sensors and their working principles are known in the art and therefore their detailed description is omitted herein. Briefly and in general, in a Hall effect sensor, a thin strip of metal has a current applied along it. In the presence of a magnetic field, the electrons in the metal strip are deflected toward one edge, producing a voltage gradient across the short side of the strip perpendicular to the feed current. In the example coding system shown in FIG. 13, a magnetic element may act or function as a binary data record, and a sensing element may act or function as a binary data reader. The ID information about the extension board can be then encoded and detected by the coding system. It should be noted that the example coding system 180 including an array of magnets and H-sensors is provided for illustration purpose. As described above, any other coding system can also be used to encode and detect identification information to an extension board. FIG. 16 depicts an end surface of an interface plate 106 showing an electrical docking interface 188. FIG. 17 depicts an end surface of an extension board 108 showing an electrical docking interface 189. The electrical interfaces 188, 189 on the interface plate 106 and extension board 108 may utilize magnetic locking and self-mating capability. Other suitable connections such as plugs and sockets can also be used as electrical interfaces. An electrical connection between the interface plate and couch top extension enables various functionalities of the couch top, including identification and verification of a couch top extension, operation of an antenna panel for a transponder tracking system, and so on.

Various embodiments of a couch top extension and couch top are described with reference to the figures. It should be noted that some figures are not necessarily drawn to scale. The figures are only intended to facilitate the description of specific embodiments and are not intended as an exhaustive description or as a limitation on the scope of the disclosure. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. The term "first" or "second" is used to distinguish one element from another in describing various similar elements and should not be construed as in any particular order unless the context clearly dictates otherwise. The term "attached," "mounted," "connected," "supported" and "coupled" and variations are used broadly and encompass both direct and indirect attachment, mounting, connections, supports and coupling.

Those skilled in the art will appreciate that various other modifications may be made. All these or other variations and modifications are contemplated by the inventors and within the scope of the invention.

What is claimed is:

1. A couch top extension, comprising:
   an extension board extending from a first end to a second end, the extension board including a first section adjacent to the first end, a second section extending from the first section, and an interface surface at an end surface of the first end, the interface surface perpendicular to a longitudinal axis extending through the extension board from the first end to the second end, the first section having a varying shape profile and the second section having a substantially uniform shape profile;
   an attachment frame attached to the interface surface, the attachment frame being configured to removably attach the extension board to a positioning device; and
   an array of magnetic elements arranged in a pattern on the interface surface of the extension board, the pattern extending outwardly away from the end surface of the first end of the extension board toward a side surface of an interface plate of the positioning device, the array of magnetic elements configured to generate electromagnetic field signals detectable by an array of sensing elements disposed on the side surface of the interface plate opposite the interface surface, the electromagnetic field signals indicative of an identification of the extension board;
   wherein the interface surface of the extension board is configured to be coupled to the side surface of the interface plate.

2. The couch top extension of claim 1, wherein a cross-section of the first section of the extension board increases in area towards the interface surface, and a cross-section of the second section of the extension board has a uniform area.

3. The couch top extension of claim 1, wherein the first section and the second section are in the form of an integral unit including an outer layer constructed from carbon fiber and a body of a low-density material sandwiched between the outer layer.

4. The couch top extension of claim 3, wherein the outer layer is constructed from a non-conductive material, the couch top extension further includes an antenna on a top surface of the extension board.

5. The couch top extension of claim 1, further comprising an indexing rail coupled to an exterior surface of a lateral side of the extension board, wherein the indexing rail is constructed from a material including a polyurethane or an epoxy polymer.

6. The couch top extension of claim 1, further comprising a load sensing device configured to detect a weight of a load on the couch top extension.

7. The couch top extension of claim 1, wherein the pattern of the array of magnetic elements is configured to indicate the identification of the extension board.

8. The couch top extension of claim 1, wherein the detectable signal is configured to be read out and provided to a control system.

9. The couch top extension of claim 1, wherein the attachment frame is configured to be between the end surface of the first end of the extension board and the side surface of the interface plate.

10. The couch top extension of claim 1, further comprising:
    a frame insert cover coupled to a top portion of the attachment frame;
    one or more front recess covers configured to be coupled to one or more front recesses defined by the end surface of the first end of the extension board, the one or more front recesses configured to receive one or more corresponding projections of the interface plate; and
    a center cover configured to be coupled to the end surface of the first end of the extension board and to cover the array of magnetic elements.

11. The couch top extension of claim 1, wherein:
  the end surface of the first end of the extension board includes a first electrical docking interface;
  the interface plate of the positioning device includes a second electrical docking interface, the first electrical docking interface and the second electrical docking interface configured to be coupled to enable identification and verification of the extension board; and
  the first electrical docking interface and the second electrical docking interface including a magnetic locking and self-mating system.

12. A couch top extension, comprising:
  an extension board extending from a first end to a second end, the extension board including an interface surface at an end surface of the first end and perpendicular to a longitudinal axis extending through the extension board from the first end to the second end; and
  an array of magnetic elements arranged in a pattern on the interface surface of the extension board, the pattern extending outwardly away from the end surface of the first end of the extension board toward a side surface of an interface plate of a positioning device, the array of magnetic elements configured to generate electromagnetic field signals detectable by an array of sensing elements disposed on the side surface of the interface plate opposite the interface surface, the electromagnetic field signals indicative of an identification of the extension board;
  wherein the interface surface of the extension board is configured to be removably coupled to the side surface of the interface plate.

13. The couch top extension of claim 12, further comprising an attachment frame attached to the interface surface of the extension board, the attachment frame being configured to removably attach the extension board to the positioning device.

14. The couch top extension of claim 13, further comprising an indexing rail along a lateral side of the extension board, the indexing rail being constructed from a material including a polyurethane or an epoxy polymer.

15. The couch top extension of claim 14, wherein the extension board comprises a first section adjacent to the first end and a second section extending from the first section, the first section having a varying shape profile and the second section having a substantially uniform shape profile.

16. The couch top extension of claim 15, wherein a cross-section of the first section of the extension board increases in area towards the interface surface, and a cross-section of the second section of the extension board has a uniform area.

17. The couch top extension of claim 16, wherein the first section and the second section are in the form of an integral unit including an outer layer constructed from carbon fiber and a body of a low-density material sandwiched between the outer layer.

18. The couch top extension of claim 17, wherein the outer layer is constructed from a non-conductive material, and the couch top extension further includes an antenna on a top surface of the extension board.

19. The couch top extension of claim 12, further comprising a load sensing device configured to detect a weight of a load on the couch top extension.

20. A couch top, comprising:
  an interface plate configured to attach to a positioning device, the interface plate including an array of sensing elements disposed on a side surface of the interface plate;
  an extension board extending from a first end to a second end, the extension board including a first section adjacent to the first end, a second section extending from the first section, and an interface surface at an end surface of the first end, the interface surface perpendicular to a longitudinal axis extending through the extension board from the first end to the second end, wherein the first section has a varying shape profile and the second section has a substantially uniform shape profile;
  an attachment frame attached to the interface surface, the attachment frame being configured to removably attach the extension board to the interface plate; and
  an array of magnetic elements arranged in a pattern on the interface surface, the pattern extending outwardly away from the end surface of the first end of the extension board toward the side surface of the interface plate, the array of magnetic elements configured to generate electromagnetic field signals detectable by an array of sensing elements disposed on the side surface of the interface plate opposite the interface surface, the electromagnetic field signals indicative of an identification of the extension board;
  wherein the interface surface of the extension board is configured to be coupled to the side surface of the interface plate.

* * * * *